US006392092B2

(12) United States Patent
McCoy et al.

(10) Patent No.: US 6,392,092 B2
(45) Date of Patent: *May 21, 2002

(54) PROCESS FOR MANUFACTURING 3-HYDROXY-3-METHYLBUTANOIC ACID (75) Inventors: Lawrence W. McCoy, Richmond, VA (US); Daniel A. Lima; Melvin E. Miller, both of Wilmington, NC (US)

(73) Assignee: Met-Rx USA, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/837,444

(22) Filed: Apr. 17, 2001

Related U.S. Application Data (63) Continuation of application No. 09/539,351, filed on Mar. 31, 2000, which is a continuation of application No. 08/685,599, filed on Jul. 19, 1996, now Pat. No. 6,090,978.

(51) Int. Cl.[7] .............................................. C07C 51/245
(52) U.S. Cl. ........................ 562/530; 562/523; 562/527
(58) Field of Search ................................. 562/530, 523, 562/527

(56) References Cited

U.S. PATENT DOCUMENTS

| 2,650,936 A | * | 9/1953 | Schmidt et al. ............. 260/528 |
| 6,090,978 A | * | 7/2000 | McCoy et al. ............... 562/530 |

FOREIGN PATENT DOCUMENTS

| GB | 647094 | * | 12/1950 |
| JP | 08198800 | * | 12/1950 |
| JP | 08198800 | | 8/1996 |
| JP | 09087270 | * | 3/1997 |

OTHER PUBLICATIONS

Pressman et al., Hydration of Unsaturated Compounds, (J.A.C.S.:62:2078–2079).*
Coffman et al., A New Synthesis of Carboxylic Acids, (J.A.C.S.:80:2882–2887).*
Pressman et al., "Hydration of Unsaturated Compounds," J.A.C.S.:62:2078–2079, Aug. 1940.
Coffman et al., "A New Synthesis of Carboxylic Acids," J.A.C.S.:80:2882–2887, Jun. 5, 1958.

* cited by examiner

*Primary Examiner*—Paul J. Killos
*Assistant Examiner*—Taylor V Oh
(74) *Attorney, Agent, or Firm*—Lyon & Lyon LLP (57) ABSTRACT

A method for manufacturing 3-hydroxy-3-methylbutanoic acid (HMB) in commercially viable amounts is disclosed. The reaction mixture cycles through an external heat exchanger while the primary reactant is added in a warmer so as to control and maintain a low temperature for the reaction mixture. The manufacturing process herein disclosed increases yield while decreasing reaction time from the synthetic processes currently practiced.

17 Claims, 3 Drawing Sheets

PROCESS FOR MANUFACTURING 3-HYDROXY-3-METHYLBUTANOIC ACID

This is a continuation of U.S. patent application Ser. No. 09/539,351, filed Mar. 31, 2000, which is a continuation of U.S. patent application Ser. No. 08/685,599, filed Jul. 19, 1996, now U.S. Pat. No. 6,090,978, all of which are incorporated herein by reference.

FIELD OF INVENTION

This invention relates to methods for manufacturing 3-hydroxy-3-methylbutanoic acid (HMB) in high yield, in large batch amounts, with high quality, and in a relatively short amount of time.

BACKGROUND OF INVENTION

Several reports have recently appeared disclosing that HMB exhibits significant efficacy for nitrogen retention and muscle building in humans. See Nissen et al., U.S. Pat. No. 5,348,979; Phillips, *Muscle Media* 2000 (October 1995), "HMB New Drug-Free Mass Builder;" these and all other references cited herein are expressly incorporated by reference as if fully set forth in their entirety herein. Promoting nitrogen retention has therapeutic importance for trauma patients and for patients showing loss of protein due to stress conditions. Moreover, administration of HMB has been reported to enhance the immune response of mammals (Nissen et al., U.S. Pat. No. 4,992,470), and to increase lean tissue development in meat-producing animals (Nissen et al., U.S. Pat. Nos. 5,087,472 and 5,028,440).

The structure of HMB is reproduced below.

Despite these several reports on the beneficial properties of HMB, this substance is currently available only in small quantities due to the lack of a suitable synthetic procedure for commercial production of HMB. In fact, during recent years, several chemical manufacturing companies have sought to develop a high output synthetic process for HMB. These attempts have been based on the reactions described in Coffman et al., *Journal of the American Chemical Society* 80:2882–2887 (1958); Wagner & Zook, *Synthetic Organic Chemistry* 422–423, 458 (1953); March, *Advanced Organic Chemistry*, Rxn. 2–43, 567 (3d ed. 1985); Blatt, *Organic Synthesis* 2:428–429, 526–527 (1943); Blatt, *Organic Synthesis* 3:302–303 (1955) Blatt, *Organic Synthesis* 5:8–9 (1973). According to this procedure, diacetone alcohol (DIA) is subjected to alkaline sodium hypochlorite oxidation to produce HMB.

In a previous attempt at producing a commercially viable procedure, an average yield of 0.26 pounds of HMB per pound of DIA was achieved, with the most efficient batch achieving a yield of 0.325 pounds of HMB per pound of DIA. The reaction was typically run in a reactor no greater than 200 gallons, with an average charge of 156 gallon of bleach and about 95 pounds of DIA, to produce about 25 pounds HMB per batch. This process was plagued by an inability to control reaction temperature, and this inability mandated the use of small batch sizes. This process moreover failed to provide access to HMB in quantities sufficient to enable therapy on humans or animals. Thus, a need exists for an HMB manufacturing process that will allow production of high quantities of high quality HMB, and will permit HMB manufacture on a large scale, has been achieved through the improvements described herein.

SUMMARY OF INVENTION

This invention is based on the unexpected discovery that, in a large scale process for production of HMB using a main reaction tank for oxidation of an HMB precursor, the batch size, yield, and quality of product can be dramatically increased by use of an external heat exchanger with constant flow loop to maintain a reaction temperature of below 15° C. The apparatus of the invention includes a reaction tank having a first temperature probe within the reaction tank, and an associated reaction mixture recycling cooling loop. The cooling loop includes an outlet passage from the reaction tank in fluid communication with an external heat exchanger, and further includes an inlet passage which connects the external heat exchanger to the reaction tank. This system allows the reaction mixture to flow from the reaction tank through the outlet passage to the heat exchanger, and then through the inlet passage back to the reaction tank. A second temperature probe is typically provided on the outlet passage. The external heat exchanger may include a cooling inlet pipe and a cooling outlet pipe which connects the external heat exchanger to an auxiliary chiller. One or more additional temperature probes may be included on the cooling inlet pipe, cooling outlet pipe, or both. Moreover, the inlet passage, which provides flow of reactant from the external heat exchanger back to the reaction tank, may be equipped with a further temperature probe.

The chemical process of the invention provides a method to produce HMB from 4-hydroxy-4-methyl-2-pentanone (diacetone alcohol, or DIA). According to the method of the invention, the reaction tank is charged with a solution of oxidant, preferably hypochlorite, hypobromite, or hypoiodite. The reaction tank and external heat exchanger are then operated in order to cool the solution to a temperature below 15° C., more preferably below 12° C., more preferably below 10° C., more preferably below 8° C., more preferably below 6° C., and most preferably below 5° C. Once the appropriate temperature has been achieved as indicated by one or more of the temperature probes, DIA is fed into the reaction tank while maintaining the solution at a temperature of 15° C. or below. During this step, it is important to carefully monitor the temperature, and to regulate the rate of addition of DIA so that the temperature does not rise above 15° C. The oxidation of DIA is an exothermic reaction, and therefore uncontrolled addition of DIA will cause a rise in temperature of the reaction mixture. If the reaction temperature is allowed to rise above 15° C., byproducts which may include acetic acid and/or diol will be formed, and this side reaction will, of course, reduce the yield and amount of the desired product HMB. We have observed that at −10° C. the ratio of HMB to diol byproduct is 5.9:1, while at 5° C. the ratio is 5.0–5.3:1, whereas when the temperature is uncontrolled, the ratio becomes 2:1. After the reaction of DIA is complete, the reaction tank is either acidified to produce HMB or treated with a salt to produce a salt thereof.

In accordance with the method herein disclosed, we have been able to achieve an average yield of 0.44 pounds of HMB per pound of DIA, a significant and unexpected 70% improvement over the earlier used process. The highest batch yield with our procedure has been 0.50 pounds of HMB per pound of DIA. Not only has yield improved, but addition of DIA can be conducted at a rate 10–20 times faster than the rate used in the earlier process. In the improvement described herein, more than ten times as much DIA was added in a 4- to 8-hour period as was added in an 8-hour period during the earlier process. This improvement in the reactant addition rate is also significant and unexpected.

In a preferred embodiment, the reaction tank is charged with hydrochloric acid after the reaction of DIA is completed, and the pH is adjusted to approximately 3.5 or lower. Thereafter, HMB is extracted with an organic solvent, and the organic solvent may be removed by vacuum distillation in order to concentrate HMB. In certain embodiments, the extraction solvent is ethyl acetate. In another embodiment, the heat exchanger is a carbate heat exchanger, and includes a cooling tank holding a cooling fluid, a cooling inlet passage, and a cooling outlet passage, all in fluid communication with the external heat exchanger. The cooling fluid can be a solution of methanol and water, and the cooling tank is optimally maintained at a temperature of lower than $-10°$ C., more preferably lower than $-20°$ C. Thus, according to the HMB manufacturing process disclosed herein, the reaction mixture may be pumped through the external heat exchanger at a rate of at least 80 gallons/minute, more preferably 90 gallons/minute, more preferably 100 gallons/minute, more preferably 110 gallons/minute or more. During charging of the tank with DIA, the rate of addition of DIA may be adjusted based on temperature readings at the first and second temperature probes, which refer to the temperature probe within the reaction tank and the temperature probe on the outlet passage.

In another embodiment, the reaction tank is equipped with an adjustable decant tube to facilitate rapid extraction of organic solvent. The adjustable decant tube includes an elongated tubular member which extends through an opening at the top of the reaction tank and down into the reaction tank, terminating in a "J" section which allows a clean decant of organic solvent. The decant tube includes, at its top portion, an attachment which allows connection of the tube to a pulley system which is used to raise and lower the adjustable decant tube within the reaction tank as described below in more detail.

BRIEF DESCRIPTION OF DRAWINGS

Reference is next made to a brief description of the drawings, which are intended to illustrate the processing apparatus for use in the method disclosed herein. The drawings and detailed descriptions which follow are intended to be merely illustrative and are not intended to limit the scope of the invention as set forth in the appended claims.

DETAILED DESCRIPTION

We have discovered that maintaining low temperatures during the production of 3-hydroxy-3-methylbutanoic acid (HMB) is an important feature of the HMB manufacturing process owing to the exothermic nature of the reaction. Methods of synthesizing HMB to date have been insufficient for producing commercially viable amounts of HMB. However, the introduction of an external heat exchanger to the process, along with the innovative injection of the primary reactant and the constant measuring of the reaction mixture temperature, allows for a significant increase in the reaction time and yield of HMB.

Figure 1:
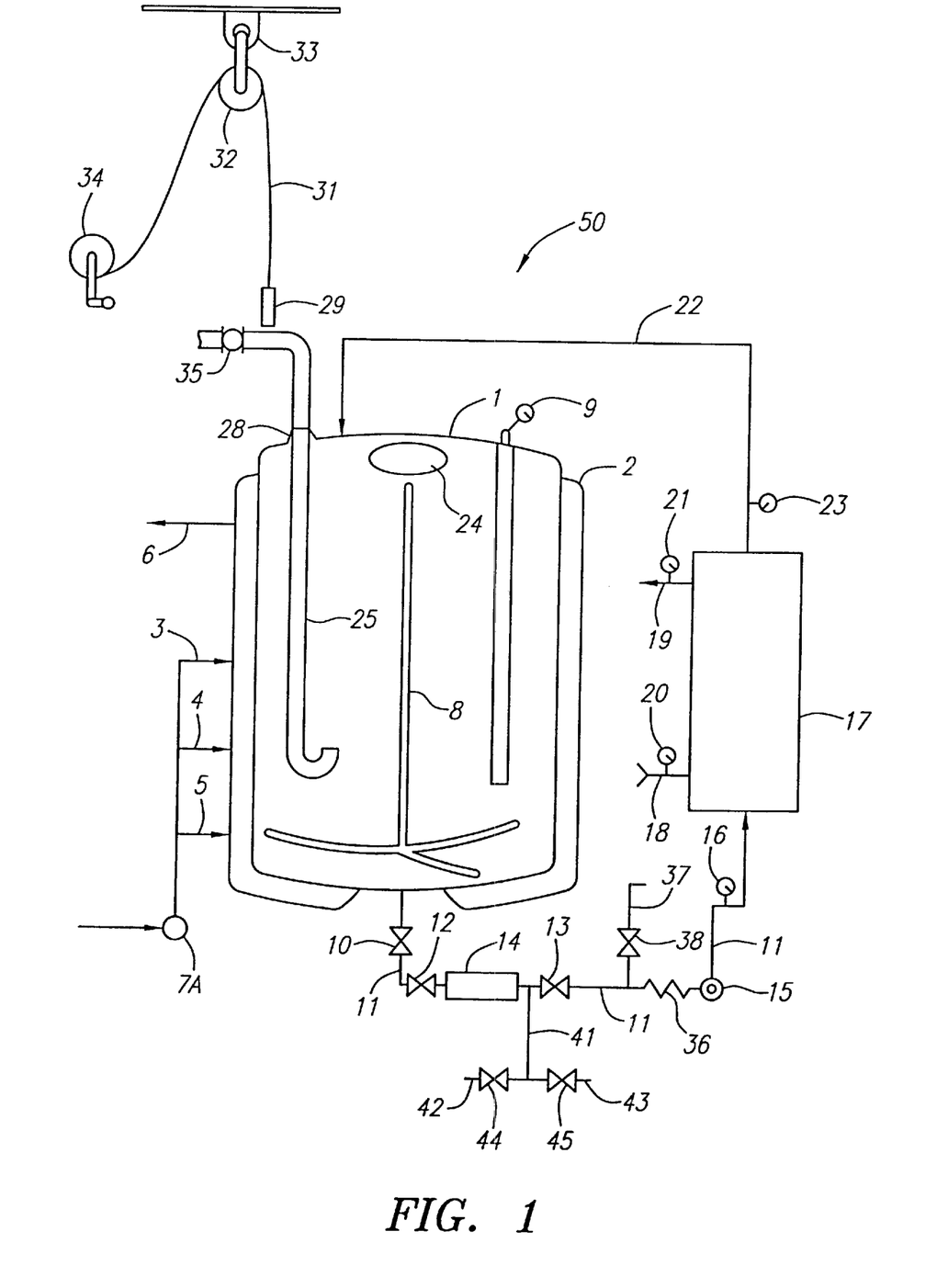
FIG. 1 is a diagram showing a reaction tank and external heat exchanger for use in a process of manufacturing HMB. This embodiment shows the decant tube containing a "J" section and hook for connection to a pulley system.

A reaction system having a recycling cooling loop as used herein is depicted in FIG. 1. The reaction mixture recycling cooling loop system 50 is responsible for controlling the temperature of the reaction mixture, and constitutes a substantial improvement for the system disclosed herein. The system is comprised of reactor 1, typically a glass-lined reactor selected to have a volume that will accommodate the quantity of reactants to be added, generally a volume of greater than 200 gallons, more preferably greater than 400 gallons, more preferably greater than 800 gallons, more preferably greater than 1,000 gallons, more preferably greater than 1,200 gallons, and for a typical batch, 1,500 gallons or more. The system also includes an external heat exchanger 17, more preferably a carbate heat exchanger, used to cool the reaction mixture. The reactor 1 is surrounded by cooling jacket 2 which has at least one cooling solution inlet 3, and possibly additional inlets 4 and 5, and a cooling solution outlet 6 to allow cooling solution to fill cooling jacket 2 and surround reactor 1. The reactor 1 also contains an agitator 8 for the purpose of mixing the contents of reactor 1. A temperature probe 9 extends into reactor 1, preferably from the top, to provide means for monitoring the temperature of the contents of reactor 1.

The reactor 1 will generally have a capacity of greater than 200 gallons, more typically greater than 300 gallons, more typically greater than 600 gallons, more typically greater than 1,000 gallons, more typically greater than 1,300 gallons, and generally 1,500 gallons or more. It will be understood that the use of a large reactor is not merely a matter of routine design selection, but is a crucial parameter for scale-up of the HMB reaction which is enabled only by use of the cooling technology which we have developed. Thus, by using previous cooling techniques, it was not possible to scale-up to large size reaction equipment as we have now disclosed. Instead, previous work in this area was limited to use of small size reactors of about 200 gallons or less because previous researchers were not able to control reaction temperatures using large scale equipment and the corresponding larger scale of reactants, as we now disclose.

Outlet passage 11 allows fluid to flow from reactor 1 to heat exchanger 17. A bottom valve 10 controls the flow of contents out of reactor 1. The outlet passage 11 passes through bottom valve 10 and connects to a Teflon® butterfly valve 12, which allows the drained contents to flow into a glass spool piece 14 providing visualization of the material flowing through outlet passage 11. Immediately downstream of glass spool piece 14 is situated inlet passage 41, which branches into passages 42 and 43. Passage 42 allows for the addition of nitrogen gas for flushing the reaction mixture recycling cooling loop. Addition of nitrogen gas through passage 42 is controlled by valve 44. Passage 43 allows for the removal of chloroform from reactor 1 and for the addition of acid to the reaction mixture recycling cooling loop. The removal of chloroform and the addition of acid is controlled by valve 45 situated on passage 43. Butterfly valve 13 is situated further downstream of inlet passage 41 along outlet passage 11.

Continuing further along outlet passage 11, inlet passage 37 allows addition of DIA as controlled by valve 38. After the juncture with inlet passage 37, outlet passage 11 passes through flex joint 36 and into centrifugal pump 15. Outlet passage 11 continues beyond centrifugal pump 15 and attaches to external heat exchanger 17. A temperature probe 16 is attached to outlet passage 11 downstream of centrifugal pump 15 and prior to the junction of outlet passage 11 with heat exchanger 17.

The external heat exchanger 17 includes inlet passage 18 to allow the flow of cooling solution from the auxiliary chiller system described below. Heat exchanger 17 also includes outlet passage 19 to allow the flow of cooling solution back to the auxiliary chiller system. A temperature probe 20 may be attached to inlet passage 18 adjacent to heat exchanger 17, and temperature probe 21 may be attached to outlet passage 19 adjacent to heat exchanger 17.

An inlet passage 22 completes the flow of material through the reaction mixture recycling cooling loop by providing fluid communication from heat exchanger 17 to reactor 1. A temperature probe 23 may be mounted on inlet passage 22 adjacent to heat exchanger 17 for the purpose of measuring the temperature of the reaction mixture as it exits heat exchanger 17.

Figure 2:
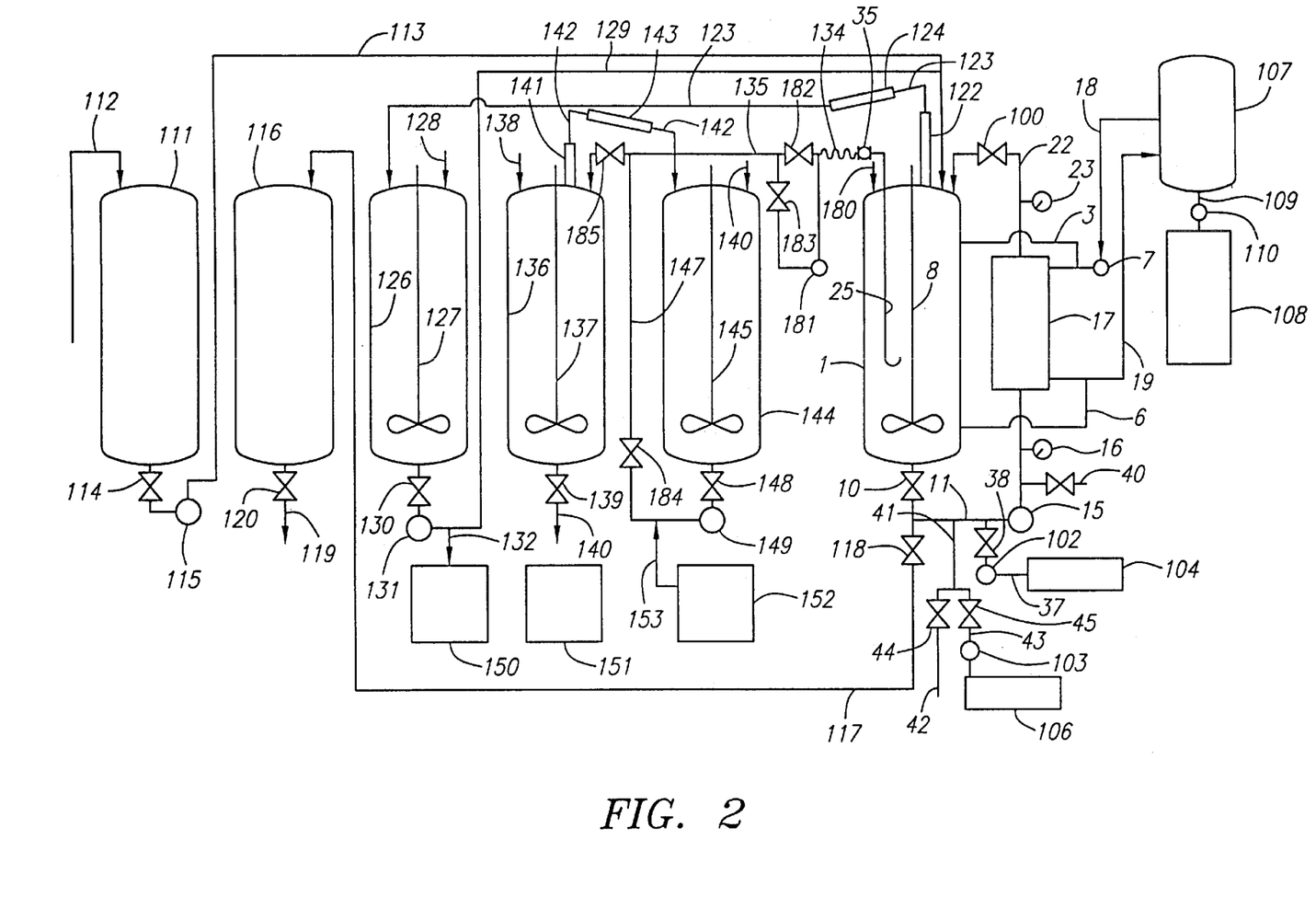
FIG. 2 is a diagram showing the process system used for the production of HMB crude oil.

A complete diagram of an HMB crude flow system is depicted in FIG. 2. Referring to FIG. 2, the auxiliary chiller system includes chiller hold tank 107 and auxiliary chiller 108. The chiller hold tank 107 provides cooling solution to external heat exchanger 17 through inlet passage 18 and to the cooling jacket 2 surrounding reactor 1 through one or more of cooling solution inlets 3, 4, and 5 (shown in FIG. 1), which branch off from inlet passage 18. Pump 7, situated along inlet passage 18, forces cooling solution through the cooling solution loop. Pump 7A (shown in FIG. 1) is also situated along inlet passage 18, immediately upstream of cooling solution inlets 3, 4, and 5, for the purpose of providing a boost to the rate of cooling solution flow, if desirable. Cooling solution returns to chiller hold tank 107 through outlet passage 19 from the external heat exchanger 17, which is joined by outlet passage 6 from cooling jacket 2. Passage 109 allows the transfer of cooling solution between chiller hold tank 107 and auxiliary chiller 108. A pump 110 situated along passage 109 transfers cooling solution between chiller hold tank 107 and auxiliary chiller 108.

The auxiliary chiller 108, chiller pump 110, and an associated generator (not shown) are turned on prior to the addition of oxidant to reactor 1 in order to pre-chill the cooling solution. The chiller maintains the temperature of the cooling solution in the chiller hold tank 107 at a sufficiently low temperature to maintain the reaction mixture at an appropriate temperature. The cooling solution is thus generally maintained at between −10 to −20° C. The cooling solution typically comprises a methanol/water mixture, more preferably ⅓ methanol and ⅔ water, more preferably 1,000 gallons of water and 632 gallons of methanol. In the preferred embodiment, the specific gravity of the cooling solution will generally be approximately 0.95, more preferably 0.9531 (30% methanol) or lower.

In use, a process of synthesizing crude HMB begins by charging the reactor 1 with a quantity of oxidant, e.g., sodium hypochlorite, sodium hypobromite, sodium hypoiodite, calcium hypochlorite, calcium hypobromite, or calcium hypoiodite. Where sodium hypochlorite is used, 12.5–15% (pH 12.0–13.5), more preferably 14.5%, sodium hypochlorite from the glass-lined oxidant bulk storage container 111 is passed through passage 113, which preferably is a dedicated plastic line. The quantity of oxidant charged into reactor 1 is preferably greater than 200 gallons, more preferably greater than 400 gallons, more preferably greater than 800 gallons, most preferably greater than or equal to 1,200 gallons. The flow of oxidant from bulk storage container 111 is controlled by valve 114 and pump 115, which is preferably an air driven plastic pump, both of which are situated along passage 113 in close proximity to bulk storage container 111. The bulk storage container 111 is filled from an external delivery source through inlet passage 112.

Referring again to reactor 1 and its associated external heat exchanger, agitator 8 and then pump 7 are turned on to circulate cooling solution through external heat exchanger 17 and cooling jacket 2. Pump 15 is then used to circulate the contents of reaction tank 1 through external heat exchanger 17, once valves 10, 12, and 13 are opened, and valves 38, 44, 45, and 118 are closed. The temperature of the oxidant is lowered to 0–5° C. by heat exchange which occurs both through the cooling jacket and the external heat exchanger. The temperature of the contents of the glass-lined reactor 1 is controlled through a combination of manipulating chiller recirculation tank flow (throttling the tank outlet valve), shutting on and off the chiller cooling loop pump 7, and adjusting booster pump 7A (shown in FIG. 1) to increase or decrease the rate of flow through the cooling loop. The chiller unit pump 110 generally remains on constantly.

Once the oxidant within reactor 1 has been chilled to below 10° C., preferably 0–5° C., the inlet temperature at temperature probe 16, and optimally, the outlet temperature at temperature probe 23, are noted. Next, diacetone alcohol, the precursor of HMB, is added to the reaction mixture recycling cooling loop from the DIA storage container 104, through inlet passage 37, passing through feed pump 102, preferably a Teflon® feed pump, and check valve 38, both of which are connected to inlet passage 37. DIA is added over a 4- to 8-hour period at a rate of approximately 0–5 pounds per minute, preferably 2.5 pounds per minute. The total amount of DIA added for one batch is typically 100 or more pounds, more preferably 300 or more pounds, more preferably 500 or more pounds, more preferably 700 or more pounds, more preferably 900 or more pounds, with an average of about 957 pounds. It will be understood that the quantity of DIA added will depend on the quantity of bleach charged to the reactor, and will typically have a ratio of about 1:12 by weight (DIA:oxidant), presuming an oxidant concentration of 12.5–15%. This ratio can also be expressed as about 1:1.2 pounds DIA to gallons of oxidant. By comparison to known techniques, DIA addition could previously be added at no more than 95 pounds over a period of 8 hours. The temperature probes 9 and 16, and preferably at least one additional probe selected from probes 20, 21, and 23, are monitored to determine how to set the rate of addition of DIA to maintain the temperature at inlet passage temperature probe 16 below 10° C., preferably between 0–5° C.

With the start of DIA addition, full cooling is in place and temperature adjustments are performed by any one of a combination of adjusting the rate of DIA addition, adjusting the rate of flow of cooling solution through the cooling loop, increasing the flow rate of the reaction mixture in the reaction mixture recycling cooling loop by adjusting pump 15, and adjusting the temperature of cooling solution in the cooling loop. In a preferred embodiment, temperature adjustments are performed solely by adjusting the rate of DIA addition. The preferred rate of DIA addition is 0–5 pounds per minute. The exotherm produced by the reaction is virtually nonexistent over the addition of the last 10% of the DIA. Therefore, the auxiliary chiller flow rate will have to be adjusted by throttling the outlet valve (not shown) for chiller hold tank 107 or shutting off the chiller cooling loop pump 7 entirely.

After DIA addition is completed, the DIA line is flushed with water. The temperature of reactor 1 is then maintained at about 3–10° C. Carbon monoxide forms in reactor 1 at this time, so that the reactor container vent (not shown) should be fully open and the manway 24 should be fully closed.

Acid (preferably hydrochloric acid; more preferably 1,700–2,120 pounds of 32% hydrochloric acid) is added to the reaction mixture from acid storage container 106 through passage 43 and through inlet passage 41, passing through feed pump 103 and check valve 45. During the acid addition, the reaction mixture recycling cooling loop continues to operate in order to provide good mixing. In one embodiment, the acid is added and the temperature is maintained at approximately 10–20° C. The pH of the reaction mixture is monitored at the recycling loop sample nozzle 40 to insure that the pH is maintained at about between 3.0–3.5, preferably 3.0–3.2. The reaction mixture is maintained at 10–20° C. for about two hours.

Further, hydrochloric acid is added in the same manner as described above, frequently checking pH and stopping between about pH 3.0 and 3.2. The reaction mixture is agitated and recycled through the reaction mixture recycling cooling loop for 10–15 minutes, and a final pH check is performed to ensure that the pH is between about 3.0 and 3.2 without dropping below about 3.0.

Bottom valve 10 is closed, and water is added to outlet passage 11 in order to flush the reaction mixture recycling cooling loop into reactor 1, and the loop is purged with a nitrogen flush added through passage 42 and inlet passage 41 as regulated by valve 44. After the reaction mixture recycling cooling loop is purged, valves 10, 12, and 13 are adjusted to close off the cooling loop, and any cooling is shut off.

Agitator 8 is rested, and the reaction mixture is allowed to settle. A haloform layer will form as a bottom layer in reactor 1. This bottom haloform layer is drained through outlet passage 11 by opening valves 10, 12, and 45, closing valve 13, and draining through passages 41 and 43.

In a preferred embodiment of the procedure, it is then desirable to strip water from reactor 1. First, a vacuum is pulled on the reactor container by applying vacuum to the receiver water strip holding tank 126. Approximately one-half of the contents in reactor 1 is distilled through outlet means 122 and outlet passage 123 into condenser 124 and continuing through outlet passage 123 into water strip holding tank 126. A portion of the distilled water strip is drummed into tote 150 (several of which may be required) at least once during the distillation since the distillation will remove many gallons of water strip, consisting primarily of water but also including varying amounts of acetic acid, acetone, and possibly haloform. Once distillation is completed, the vacuum on the reactor 1 should be broken with nitrogen from nitrogen inlet 180.

Subsequent to the water strip step, the contents of reactor 1 are cooled to 25° C. with agitation, creating a thick salt slurry of product. Next, hydrochloric acid is added through the top of reactor 1 to perform a final pH adjustment to about 3.0–3.2. The product mixture is mixed with agitator 8 for 10–30 minutes after the final pH adjustment to ensure the maintenance of the pH at about 3.0–3.2.

The product is then extracted from the salt slurry with organic solvent, preferably a polar organic solvent that is not miscible with water, most preferably ethyl acetate. Agitator 8 is shut off and decant tube 25 is lowered to the level of the liquid. A mark is made in relation to the decant tube 25 so that the decant tube 25 can be returned to the same position once the product has been extracted into the organic solvent. All lines, including passages 135, 142, and 147, which will contain organic solvent are grounded and purged with nitrogen. Organic solvent is added to reactor 1 from organic solvent recovery tank 144 through inlet passage 147, discharging from the recovery tank 144 and leading through valve 148 and pump 149 and eventually into reactor 1, or from a source of fresh organic solvent 152 through an inlet means 153 into the inlet passage 147 leading to reactor 1. The decant tube 25 is raised above the liquid level and agitator 8 is activated. Agitator 8 is then turned off and the contents of reactor 1 allowed to settle. The decant tube 25 is then lowered to the interface between the organic and aqueous layers. Pump 181 is turned on, valves 182 and 184 are closed, valves 183 and 185 are opened, and organic solvent is decanted to organic solvent extraction tank 136 from the decant tube 25 through dip tube sighting glass 35, flexible hose 134, and outlet passage 135.

The organic solvent extraction may be performed one, two or several more times, checking the pH before each extraction. A pH adjustment may be appropriate and may be performed by adding acid through the top of the reactor 1 since the pH usually rises as the result of an extraction. After the extraction procedure has been completed, reactor 1 contains salt waste which is redissolved by adding into reactor 1 the water distilled in the earlier water strip step from the water strip holding tank 126. The mixture of the water and salt waste is stirred with agitator 8 to ensure that all salt is in solution. The mixture is then heated if all salt does not go into solution immediately, and water may be added. After the salt waste has been brought into aqueous solution, the contents are heated to about 60° C. under full vacuum to remove any residual organics. The contents of reactor 1 are then cooled to about 25° C. and pumped out by opening bottom valve 10 and valve 118, allowing the salt solution to flow through passage 117 into the waste tank 116. Waste salt solution gathered in waste tank 116 is periodically transferred to bulk waste haulers through outlet means 119 by opening valve 120.

Now that the HMB product is in solution with organic solvent in extraction tank 136, a cut is made in extraction tank 136 by opening valve 139 and allowing any water layer which was inadvertently transferred to extraction tank 136 to flow from the tank through outlet passage 140. Next, extraction tank 136 and recovery tank 144 are run under vacuum to recover the organic solvent. During this step, organic solvent from extraction tank 136 will distill through outlet means 141 into condenser 143, and continuing through outlet passage 142, into recovery tank 144. After this preliminary distillation of organic solvent, approximately 450–500 pounds, or approximately 40–50 gallons, of HMB crude oil will remain in extraction tank 136. This HMB crude oil is thereafter transferred to one or more product tote bins 151 by opening valve 139 and allowing the crude oil to flow from extraction tank 136 through outlet passage 140.

Figure 3:
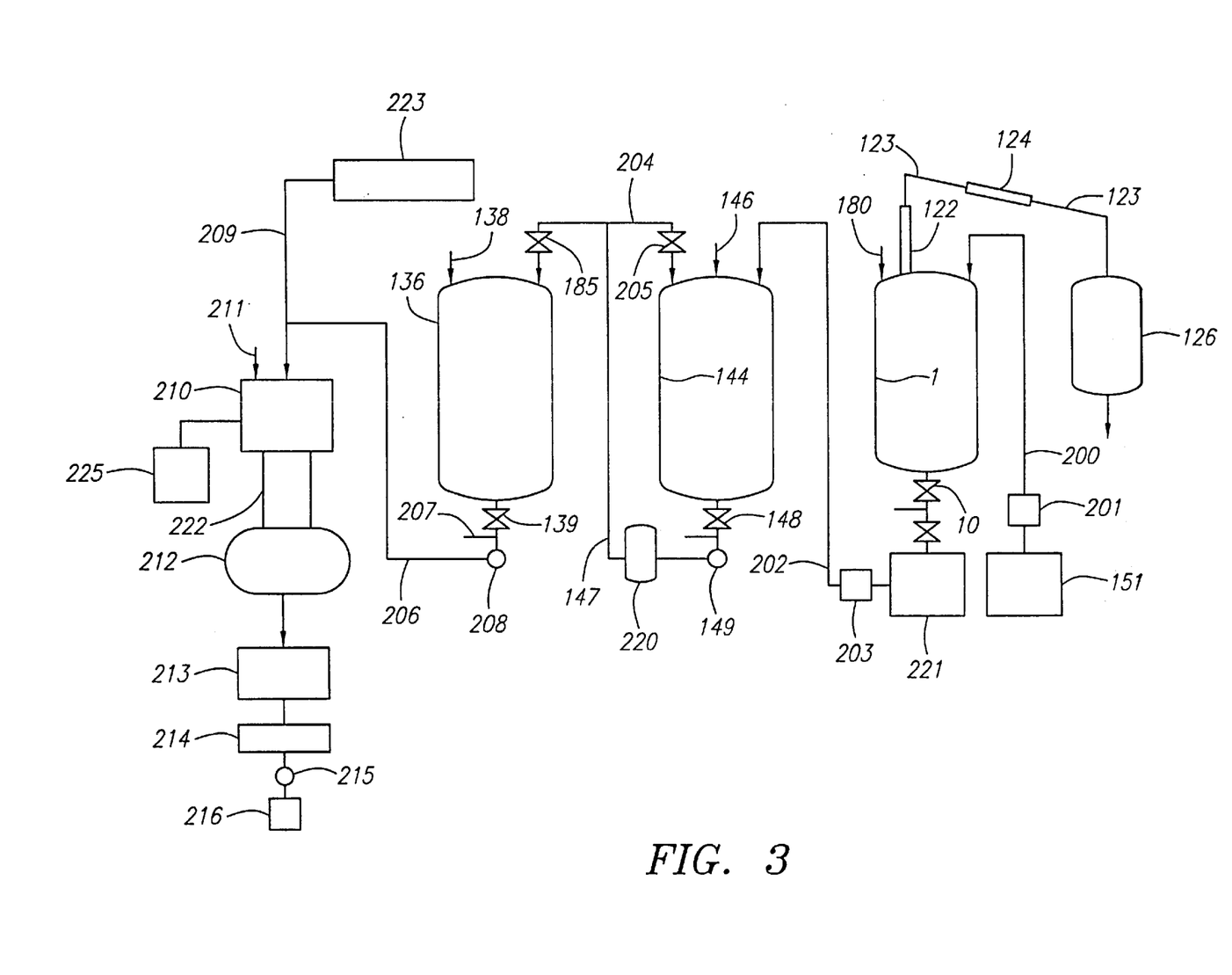
FIG. 3 is a diagram showing the process system used for the production of finished HMB from the HMB crude oil.

After the preliminary organic solvent extraction has been completed, the finished process phase begins. Several batches of HMB crude oil are charged into reactor 1 from tote bins 151 through bag filter 201 as illustrated in FIG. 3 to remove small amounts of residual salt. Reactor 1 is heated under full vacuum to about 60–70° C. to distill residual organic solvent into water strip holding tank 126. Once the organic solvent take-off approaches zero, a nitrogen sparge is performed through bottom valve 10 to sweep residual organic solvent from the crude. A sample is collected from the contents remaining in reactor 1 to check for organic solvent by high performance liquid chromatography analysis.

Once the product has been approved as free of organic solvent, HMB crude oil is removed from reactor 1 and transferred into a clean tote bin 221. After obtaining a net weight of the unfinished product, a quantity of the unfinished product is collected to be used later in the finishing process for pH adjustment, if necessary. Thereafter, 5,000–9,000 pounds of ethanol or toluene, preferably ethanol, are transferred from drums or an ethanol/toluene recovery tank (not shown) into reaction tank 144 via clean pump or vacuum. Agitator 145 is used to stir the ethanol, ensuring that the system is fully grounded from drum through connection. The ethanol is heated to about 20° C. If the ethanol that is being used is fresh ethanol, as opposed to recovered ethanol, then water is added to recovery tank 144, according to the formula wherein the pounds of water to be added is determined by multiplying the pounds of ethanol by 0.063. If the ethanol being used is recovered ethanol, this water may not be added.

The unfinished/crude HMB product is transferred to recovery tank 144 from tote bin 221 through filter 203. Recovery tank 144 is heated to about 30° C. Thereafter, 500–800 pounds, preferably 50 pounds at a time, of calcium hydroxide, calcium oxide, calcium carbonate, or calcium acetate, more preferably calcium hydroxide USP, is added to recovery tank 144 at a controlled rate and under cooling to keep the temperature of the contents between about 30–45° C., more preferably 40–45° C. The temperature of about 40–45° C. is desirable since the mixture gels below 30° C. Maintaining the temperature at 45° C. will likely require adding chilled water in the cooling jacket (not shown) surrounding recovery tank 144 as needed.

The pH is adjusted to about 6.5–7.0 using the calcium hydroxide. The pH increases quickly during this adjustment, so caution must be taken in approaching a pH of 6.5–7.0. If the pH goal is surpassed, the HMB crude saved from earlier in the process may be used to adjust the pH downward into the desired range. Once the pH adjustment is completed, the recovery tank 144 is fully purged and the temperature maintained at 45° C.

In the meantime, extraction tank 136 is prepared to receive the filtered mixture from recovery tank 144. A vacuum cycle nitrogen purge is performed on extraction tank 136 prior to filtration. Approximately 10–15 pounds of celite is added to the mixture in recovery tank 144. Next, the mixture is filtered by opening valve 148, turning on pump 149, and allowing the mixture to flow through filter 220 situated along passage 147 and through passage 204 and open valve 205 to recycle into recovery tank 144. Filter 220, in its preferred embodiment, is an 18-inch, 12-tray Niagara filter preheated with atmospheric steam. The reaction mixture is recycled through filter 220 and recovery tank 144 until a clear filtrate is established. Throughout the filtration process, recovery tank 144 is maintained at a temperature of approximately 45° C., and atmospheric steam is periodically charged into the jacket (not shown) of filter 220. If the filtration takes longer than one hour, filter 220 is blown with nitrogen and replaced. After the filtrate becomes clear, valve 205 is closed and valve 185 opened so that the mixture is transferred from recovery tank 144 to extraction tank 136 through passage 147. Throughout the transfer, the temperature of extraction tank 136 is maintained at approximately 45° C. To ensure that all product has been transferred from recovery tank 144 to extraction tank 136, the filter is blown with nitrogen through to extraction tank 136.

Once the transfer to extraction tank 136 is complete, the reaction mixture is checked to ensure that the filtration was satisfactory. If not satisfactory, the reaction mixture is pumped back to recovery tank 144 and refiltered. Next, the temperature of the reaction tank is cooled to about 35° C. After the temperature adjustment, the batch is seeded with seed crystals of HMB. Subsequent to the seeding, the temperature is further cooled to about 30° C. over two hours, as the product begins precipitating, forming a milky white slurry. The reaction mixture is further cooled slowly to about 20–25° C. over four additional hours. In the final cooling step, the temperature of the reaction mixture is cooled slowly to about 0–5° C. over two hours and maintained at 5° C. or less for an additional hour.

In preparation for the finishing steps, centrifuge 210 is fully purged with nitrogen through nitrogen inlet 211, and a dedicated tote bag 212 is mounted on drop chute 222. The ethanol wash tank 223 is prepared at a temperature of about 0–5° C. for each batch wash. Ethanol is added to each centrifuge load through passage 209. The filtrate is directed to the filtrate tank 225 where it is periodically checked for solids before being sent to the used ethanol drums for disposal.

The batch is centrifuged, generally in several loads, with each tote bag receiving one centrifuge load. Once the entire batch has been centrifuged, the batch is charged into dryer 213 and dried for approximately 4 hours before sampling. When the sample shows a loss on drying of about 0.1% or less, dryer 213 is unloaded to blender 214 and then through screen 215, preferably a 600-micron screen, to delump the material. The resulting product from one batch according to this procedure will yield 30 or more pounds of finished HMB, more typically 50 or more pounds, more typically 100 or more pounds, more typically 200 or more pounds, more typically 300 or more pounds, more typically 400 or more pounds, with an average amount of HMB of approximately 421 pounds. Based on the amount of DIA used, the yield is generally 0.330 or more pounds of HMB per pound of DIA charged, more typically 0.35 or more pounds of HMB per pound of DIA charged, more typically 0.4 or more pounds of HMB per pound of DIA charged, with an average yield of 0.44 pounds of HMB per pound of DIA charged. The final material is drummed as one lot into 30-gallon leverpaks with plastic liners and labeled as HMB finished. A sample of the finished product is provided to the laboratory.

EXAMPLE

A. Conducting the Reaction

To begin the procedure, the auxiliary chiller, chiller pump, and associated generator were turned on approximately 275 minutes prior to the charging of bleach into the reactor. The methanol/water solution exhibited a specific gravity of 0.935. After the cooling solution exhibited a temperature of 18° F. (−10° C.) or less at the chiller inlet temperature probe, 1,200 gallons of 12.5–15% (pH 12.0–13.5) sodium hypochlorite was charged into the reactor to begin the reaction procedure.

The agitator and the recycling cooling loop pump were turned on, and the temperature of the sodium hypochlorite was lowered to 0–5° C. After the target temperature for the sodium hypochlorite was reached, 957 pounds of diacetone alcohol was added at a rate of 1.3–2.9 pounds per minute. After DIA addition was completed, the DIA line was flushed with approximately 5 gallons of de-ionized water. The temperature of the reactor was then maintained at 3–10° C. for 30 minutes.

After 30 minutes, approximately 2,120 pounds of 32% hydrochloric acid was added to the reaction mixture. The acid was added at a rate of approximately 50–100 pounds per minute. At the completion of the acid addition, the reaction mixture was maintained for 30 minutes at 10–20° C. while the pH was adjusted to 3.0–3.2 by adding approximately 510 pounds of 32% hydrochloric acid. Again, the acid was added at a rate of about 50–100 pounds per minute. The reaction mixture was then agitated for 10 minutes, after which the pH was determined to be 3.20.

After approximately 20 minutes, the auxiliary chiller was shut down, while the cooling solution recirculating pump remained on for an additional 10 minutes. Subsequently, the cooling solution pump and the reaction mixture recycling pump were shut down. The reactor bottom valve was closed and the reaction mixture recycling cooling loop was flushed with water and then with a nitrogen blow. Next, the cooling solution flow to the reactor jacket was shut down and blown. The reactor agitator was shut off and the reaction mixture was allowed to settle for approximately 20 minutes. The chloroform layer which formed on the bottom of the reactor was drained through the reactor bottom valve, generating approximately 848 pounds of chloroform waste stored in 2 drums, to both of which 4 ounces of soda ash and 4 ounces of ethanol were added.

B. Isolating the HMB Crude Product (1) Water Strip

The next step in the process involved stripping water from the reactor. First, a full vacuum was pulled on the reactor container to 26–27 inches of water (less than 200 mmHg). The reactor was heated with agitation to a distillation temperature of less than 70° C. Approximately 15 gallons of water was distilled to a glass receiver, drummed out, and labeled. A total of approximately 750 gallons was distilled from the reactor to a 600-gallon stainless steel water strip holding tank, 250 gallons of which was drummed out into a tote bin.

After the water strip was completed and shut down, the contents of the reactor were cooled to approximately 25° C. using agitation and the cooling jacket. Next, approximately 270 pounds of 32% hydrochloric acid was added through the top of the reactor to adjust the pH to 3.18. The product mixture was agitated for 10 minutes and no additional hydrochloric acid was necessary for addition since the pH had remained at 3.18.

(2) Product Extraction

The next step in the process involved extracting the product from the aqueous salt slurry with ethyl acetate. After the agitator was shut off, the decant tube was lowered to the level of the liquid, approximately 77 inches, and a mark was made in relation to the decant tube so that the decant tube could be returned to the same position once the product had been extracted into the ethyl acetate. The reactor was purged with nitrogen to an oxygen level of 8% or less. Approximately 500 gallons of ethyl acetate was added to the reactor from a 2,500-gallon stainless steel ethyl acetate recovery tank or from drums. The decant tube was raised to the full up position and the agitator was turned on for 30 minutes. After 30 minutes, the agitator was turned off and the contents of the reactor were allowed to settle for 20 minutes. The decant tube was then lowered the 77 inches to the interface between the organic and aqueous layers. The upper ethyl acetate layer was then decanted to the 2,000-gallon stainless steel ethyl acetate extraction tank.

The ethyl acetate extraction was performed two more times. In the latter two extractions, after the 30-minute agitation step, 32% hydrochloric acid was added to adjust the pH to the 3.0–3.2 range. In the second extraction, in which 500 gallons of ethyl acetate was added, the pH was adjusted to 3.2 by adding 50 pounds of hydrochloric acid. In the third extraction, in which 400 gallons of ethyl acetate was added, the pH was adjusted to 3.10 by adding 15 pounds of hydrochloric acid. After each of the three extractions, a quart sample was collected and labeled with the batch number and extraction number. After the third extraction, a clean cut was made because the third extraction was the final decant.

(3) Salt Layer Removal

After the three extractions were performed, the reactor contained salt waste. The water distilled from the reactor in the earlier water strip step was added back to the reactor from the water strip holding tank and the tote bin in order to redissolve the salt waste remaining in the reactor. The mixture of the water and the salt waste was heated to about 60° C. under vacuum to remove residual organics, and the contents were then cooled to 25° C. The waste salt solution was pumped to a 9,500-gallon stainless steel waste tank, and a 4-ounce sample was collected during the transfer.

(4) Ethyl Acetate Recovery and HMB Crude Isolation

Approximately 1,400 gallons of ethyl acetate containing the product was accumulated in the ethyl acetate extraction tank. Approximately 10–20 pounds of water which had been inadvertently transferred during the decanting steps was drained from the bottom of the ethyl acetate extraction tank. Next, a mild vacuum of 12–15 inches of mercury was pulled on the extraction tank and recovery tank system. The extraction tank was heated with mild steam not exceeding a temperature in the extraction tank of 70° C. The vacuum and heat caused distillation of ethyl acetate into the recovery tank. The residue remaining in the extraction tank after the distillation was approximately 1,508 pounds of HMB crude oil. The HMB crude oil was thereafter transferred to a product tote bin from the extraction tank, and a 4-ounce sample was collected and labeled.

C. Finished HMB Preparation

The extraction tank was inspected for general cleanliness. Five batches of HMB crude oil, a total of 6,398 pounds, generated as in the example above were charged into the reactor from tote bins through a $10\mu$ bag filter to remove small amounts of residual salt. Next, the best possible vacuum was pulled on the reactor to distill the residual ethyl acetate into the water strip holding tank. The temperature of the reactor was maintained at less than 60° C., and in this case, at the start of the distillation, the temperature was 22° C. and the vacuum was 26 inches of mercury (100 mm of vacuum), while the temperature at the end of the distillation was 56° C. and the vacuum was 26 inches. A nitrogen sparge was conducted next, beginning at 56° C. and 26 inches. The HMB crude oil was transferred to two clean tote bins, providing a net weight of 2,491 pounds. Two 5-gallon pails of the HMB crude oil was also collected for use later in the procedure. Eight drums of ethyl acetate were drummed off from the water strip holding tank.

The HMB crude oil earlier transferred to tote bins for weighing was recharged into the reactor. Recovery tank 144 was washed and then cleaned with several vacuum cycles and with jacket steam to eliminate ethyl acetate odor. Twenty-one drums (approximately 7,560 pounds) of ethanol SD3A was charged into recovery tank. The HMB crude oil was then transferred from the reactor to the recovery tank through a $10\mu$ bag filter.

Next, the recovery tank agitator was used to stir the ethanol/HMB crude oil mixture while it was heated to 20° C. The following step comprised adding 66 gallons of de-ionized water to the recovery tank. Thereafter, 622 pounds of calcium hydroxide USP was added to the recovery tank at a controlled rate, keeping the temperature of the contents between 30° C. and 45° C., and adjusting the final pH to 6.73. The HMB crude saved from earlier in the process was not used to adjust the pH because the target range (6.5–7.0) was achieved without overshooting. Once the pH adjustment was completed, the recovery tank was fully purged with nitrogen and the temperature was maintained at between 30–45° C. The temperature was then maintained at 50° C. for one hour. Next, approximately 26 pounds of celite was added to the recovery tank, and the contents were agitated for 10 minutes.

The extraction tank was set up to receive filtered solution from the recovery tank by performing a vacuum cycle nitrogen purge, making sure no ethyl acetate odor remained in the extraction tank. The jacketed 18-inch, 12-tray, stainless steel filter with filter pads was prepared, ensuring that the filter was changed prior to processing the current batch. Before filtering, three drums (approximately 1,080 pounds) of ethanol was added to the reaction mixture.

The mixture was filtered at 50° C. from the recovery tank to the extraction tank until a sample from the loop demonstrated a clear filtrate. Once the transfer to the extraction tank was completed, the temperature of the contents of the tank was adjusted to 35° C. and 28 pounds of seed crystals were added. Subsequent to the seeding, the temperature was maintained at 35° C. for two hours. At approximately 33° C., the contents of the tank began to turn milky. Next, the extraction tank was cooled slowly to 20° C. over one hour and maintained at 20° C. for an additional hour. In the final cooling step, the temperature of the extraction tank was cooled slowly to 5° C. over two hours and maintained at 5° C. for an additional hour.

The batch was then centrifuged in ten loads at 600 rpm, washing each load with approximately 100 gallons of ethanol. The filtrate containing the HMB product was directed to the filtrate tank where it was periodically checked for solids before being sent to the used ethanol drums for disposal. Once the entire batch had been centrifuged, the batch was charged into the dryer and dried at full flow for 24 hours at 45–50° C. before sampling. The first dryer sample showed an LOD of 0.1% or less. The dryer was then unloaded to the blender and then to the screener to delump the material. The final material was drummed as one lot into 30-gallon lever-paks with plastic liners for a total net weight of 2,200 pounds.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. In a large scale reaction, a process for manufacturing 3-hydroxy-3-methylbutanoic acid or a salt thereof, comprising the steps of:

providing a large scale reaction system comprising a reactor, an external heat exchanger connected to the reactor, and an inlet passage connected to the external heat exchanger and the reactor;

charging the reaction system with a solution of oxidant;

cooling the solution of oxidant by pumping the solution of oxidant through the external heat exchanger;

feeding into the reaction system a large scale amount of 4-hydroxy-4-methyl-2-pentanone; and recovering 3-hydroxy-3-methylbutanoic acid.

2. The process of claim 1, wherein the solution of oxidant is cooled to and maintained at a temperature below 15° C.

3. The process of claim 1, wherein the solution of oxidant is selected from the group consisting of hypochlorite and hypobromite.

4. The process of claim 2, further comprising the step of charging the reaction system with acid.

5. The process of claim 4, wherein the step of charging the reaction system with acid includes charging the reactor with hydrochloric acid and adjusting the pH to approximately 3.5 or lower.

6. The process of claim 2, further comprising the steps of:

extracting 3-hydroxy-3-methylbutanoic acid with an organic solvent; and concentrating 3-hydroxy-3-methylbutanoic acid by vacuum distillation.

7. The process of claim 6, wherein the organic solvent is ethyl acetate.

8. The process of claim 2, wherein the external heat exchanger is a carbate heat exchanger.

9. The process of claim 2, wherein the external heat exchanger includes a cooling tank holding a cooling fluid, a cooling inlet passage, and a cooling outlet passage, all in fluid communication with the external heat exchanger.

10. The process of claim 9, wherein the cooling fluid is a solution of methanol and water, and wherein the cooling tank is maintained at a temperature of lower than −10° C.

11. The process of claim 10, wherein the cooling tank is maintained at a temperature of lower than −20° C.

12. The process of claim 2, wherein the reactor has a capacity of at least one thousand gallons.

13. The process of claim 2, wherein the step of cooling the solution of oxidant includes the step of pumping the solution of oxidant through the external heat exchanger at a rate of at least 80 gallons/min.

14. The process of claim 2, wherein the step of feeding into the reaction system a large scale amount of 4-hydroxy-4-methyl-2-pentanone includes the step of adjusting the rate of addition of 4-hydroxy-4-methyl-2-pentanone based on temperature readings from the reactor.

15. The process of claim 6, wherein the reactor further includes an adjustable decant tube to facilitate rapid extraction with organic solvent.

16. The process of claim 2, wherein a total of 100 pounds or more of 4-hydroxy-4-methyl-2-pentanone is fed into the reaction system.

17. The process of claim 1, wherein the step of feeding into the reaction system a large scale amount of 4-hydroxy-4-methyl-2-pentanone is performed while maintaining the solution of 4-hydroxy-4-methyl-2-pentanone and oxidant at a temperature below 15° C.

* * * * *